US00PP24934P3

(12) United States Plant Patent
Rautenbach

(10) Patent No.: US PP24,934 P3
(45) Date of Patent: Sep. 30, 2014

(54) ORANGE TREE NAMED 'CARNINKA'

(50) Latin Name: *Citrus sinensis*
Varietal Denomination: Carninka

(75) Inventor: Daniel Frederich Rautenbach, Patensie (ZA)

(73) Assignee: Citrogold (Pty) Ltd, Stellenbosch (ZA)

( * ) Notice: Subject to any disclaimer, the term of this patent is extended or adjusted under 35 U.S.C. 154(b) by 38 days.

(21) Appl. No.: 13/385,675

(22) Filed: Feb. 27, 2012

(65) Prior Publication Data

US 2013/0227751 P1 Aug. 29, 2013

(51) Int. Cl.
*A01H 5/00* (2006.01)

(52) U.S. Cl.
USPC ..... Plt./202

(58) Field of Classification Search
USPC ..... Plt./202
See application file for complete search history.

(56) References Cited

U.S. PATENT DOCUMENTS

PP21,224 P2 * 8/2010 Grosser et al. ..... Plt./202
PP21,535 P2 * 11/2010 Grosser et al. ..... Plt./202

OTHER PUBLICATIONS

ES Karninka UPOV PLUTO Citation for 'Karninka' Jun. 20, 2012.*
ZA Karninka UPOV PLUTO Citation for 'Karninka' Nov. 6, 2012.*
QZ Karninka UPOV PLUTO Citation for 'Karninka' Dec. 15, 2010.*

* cited by examiner

*Primary Examiner* — Wendy C Haas
(74) *Attorney, Agent, or Firm* — Michelle Bos

(57) ABSTRACT

A new and distinct variety of sweet orange tree (*Citrus sinensis*) named 'Carninka'. 'Carninka' is notable for its firm, late maturing fruit.

4 Drawing Sheets

Genus and species: *Citrus sinensis.*
Variety denomination: 'Carninka'.

CROSS-REFERENCE TO RELATED APPLICATIONS

None

BACKGROUND AND SUMMARY OF THE VARIETY

The new orange tree 'Carninka' originated as a whole tree mutation of a 'Palmer' navel orange tree (not patented). The mutation was discovered in 2005 in a commercial orchard of 'Palmer Navel' trees on 'Swingle' citrumelo rootstock (not patented) at Patensie, South Africa, and was distinguished by its markedly late maturity as compared to other navel orange trees, even those considered to be late-maturing. Asexual propagation by budding was first carried out in 2005 at Patensie to determine whether the desirable characteristics of the mutation would carry through to asexually propagated progeny. It has been found that the desirable characteristics are in fact reproduced through asexual propagation, and remain stable through successive generations.

'Carninka' is a new and distinct orange tree notable for its late maturity as compared to 'Palmer Navel' and other late maturing orange varieties.

BRIEF DESCRIPTION OF THE PHOTOGRAPHS

Figure 1:
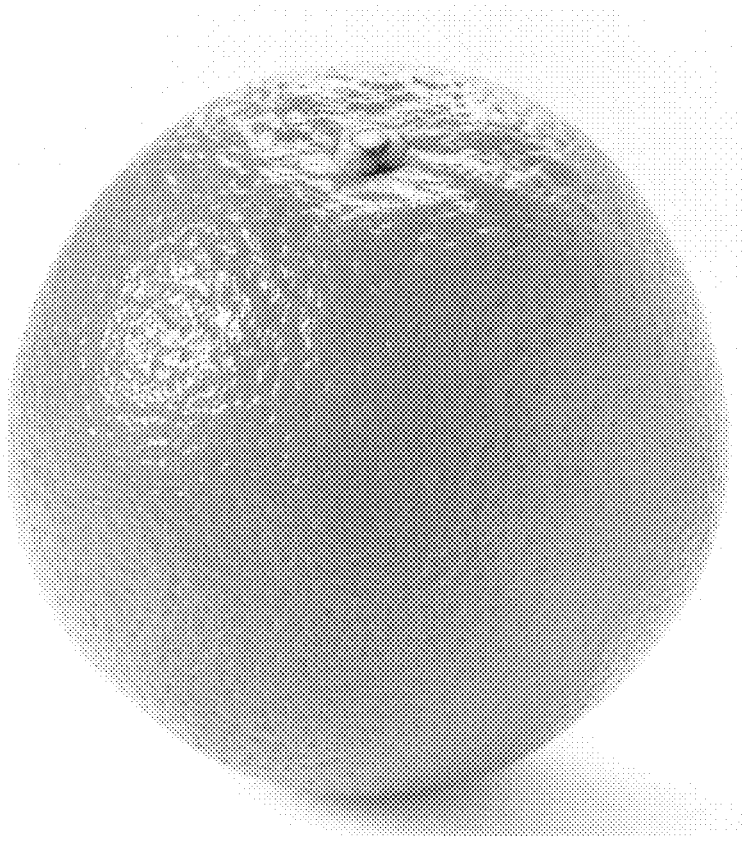
Figure 2:
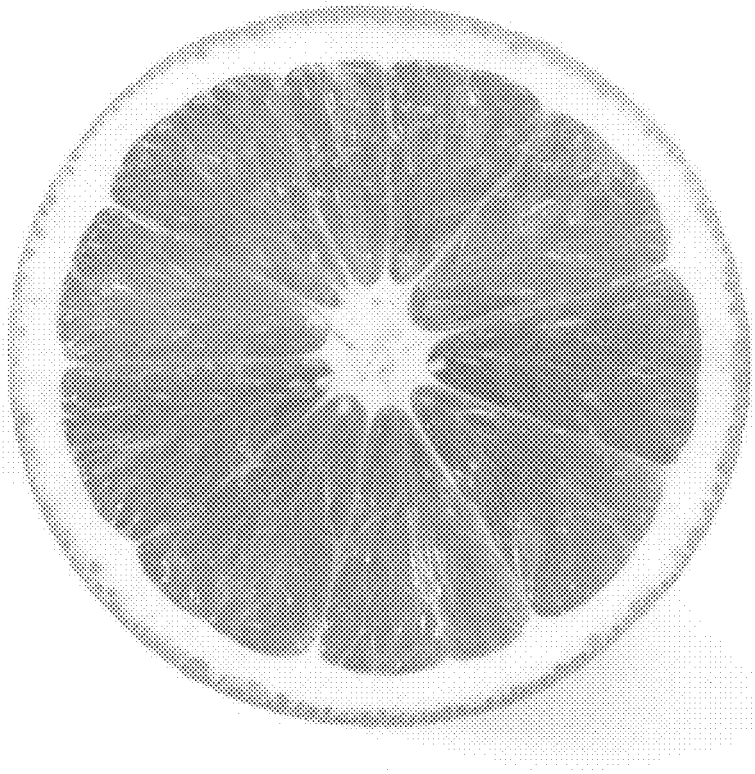
Figure 3:
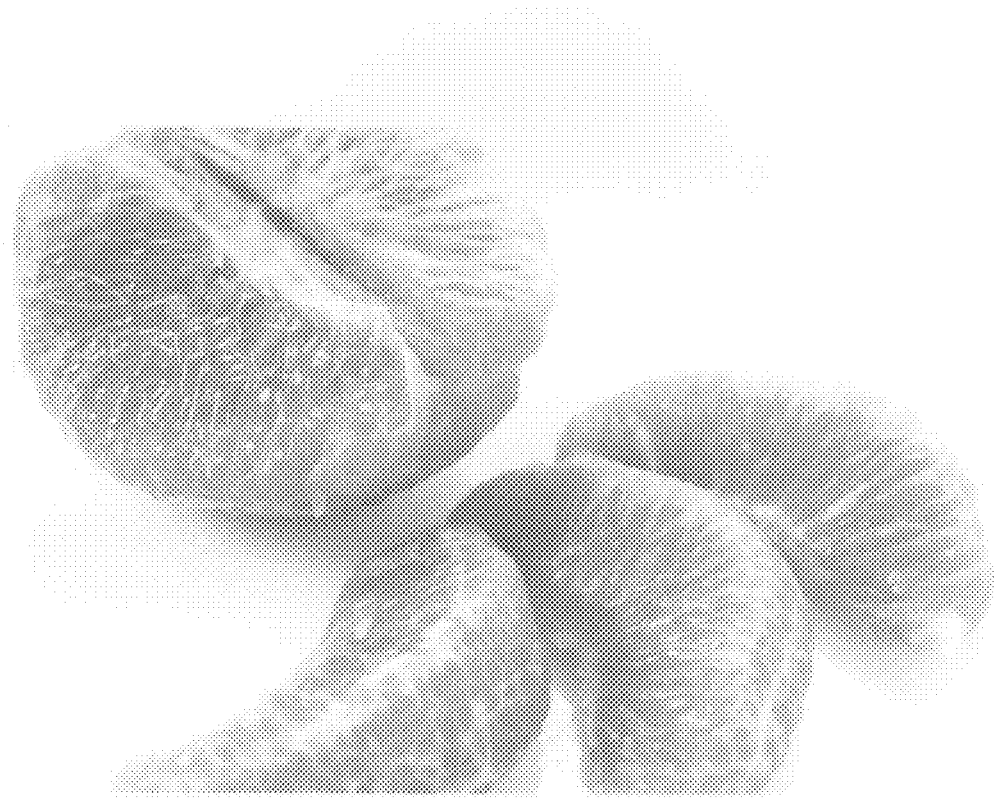
Figure 4:
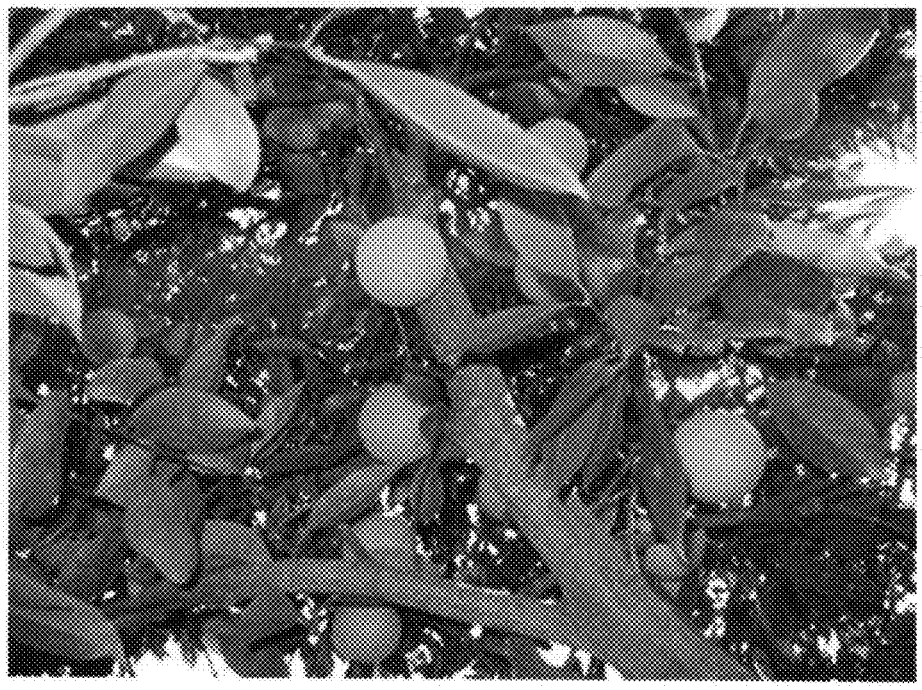

FIG. 1 shows the fruit of the new variety;
FIG. 2 shows a sectioned fruit of the variety;
FIG. 3 shows fruit segments of the new variety; and
FIG. 4 shows the tree and leaves of the new variety.

The colors of the claimed variety may vary with lighting conditions. Color characteristics of the variety should therefore be determined with reference to the observations described herein, rather than from these illustrations alone.

DETAILED BOTANICAL DESCRIPTION

The following detailed botanical description is based on observations of the original tree of the variety, planted in 1983 and grown on 'Swingle' citrumelo rootstock. Observations were recorded and photographs taken during the 2008, 2009 and 2010 growing seasons at Patensie, South Africa. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants of the new variety may vary from the stated average. Colors are described with reference to The Royal Horticultural Society Colour Chart (2007) (R.H.S.) and the Citrus Research International Colour Prints (Nelspruit, South Africa, 2005).

Tree:

*Vigor.*—Precocious in juvenile phase; vigor of mature trees comparable to 'Palmer' navel.
*Density of canopy.*—Average to dense.
*Habit.*—Spreading.
*Height.*—1.6 m, similar to 'Palmer' navel.
*Spread.*—Medium, 1.3 m.
*Trunk diameter.*—17 mm (one of two stems, 30 cm above graft).
*Bark texture.*—Reasonably smooth, typical of navel orange trees.

*Bark color*.—Dark grey 201B with green striae, typical of navel orange trees.
*Tendency toward alternate bearing*.—None noted.
*Winter hardiness*.—Sensitive below −2° C. (similar to 'Washington' navel).
*Chilling requirement*.—None.
*Drought tolerance*.—Similar to 'Washington' and 'Palmer' navel.

Branches:
*Length*.—30 cm.
*Diameter*.—5 mm.
*Crotch angle*.—45° maximum.
*Bark color*.—Gray 201B.
*Bark texture*.—Smooth.
*Thorns*.—Sparse thorns observed during initial growth phase following shoot tip grafting; a few thorns appear in the first few growth flushes of first generation material after shoot tip grafting; thorns absent in mature trees.
*Thorn length*.—Short, up to about 8 mm Current year shoot length Up to 250 mm.
*Current year shoot color*.—Light green 150B.

Flowers:
*Quantity of blossoms per cluster*.—Up to 4.
*Blossom diameter*.—49.5 mm.
*Blossom depth*.—27.0 mm (base of sepal to apex of petal).
*Pollen*.—Present.
*Sepal length*.—5.71 mm.
*Sepal width*.—4.29 mm.
*Sepal shape*.—Acute.
*Sepal margin*.—Entire (smooth).
*Sepal color—upper surface*.—Yellow 8A with white margins.
*Sepal color.—lower surface*.—Yellow 8A with white margins.
*Quantity of petals per flower*.—Generally 5.
*Petal shape*.—Acute, elongated, stellate.
*Petal apex*.—Acute.
*Petal margin*.—Entire.
*Petal length*.—25.92 mm.
*Petal width*.—744 mm.
*Petal color—upper surface*.—White NN155D.
*Petal color—lower surface*.—White NN155D with yellow dots.
*Date of first bloom*.—10 October.
*Date of full bloom*.—15 October.
*Date of first fruitlet fall*.—14 November.
*Pedicel length*.—10.66 mm.
*Pedicel diameter*.—1.66 mm.
*Pedicel color*.—Light green 150B.
*Pistil quantity per flower*.—1.
*Pistil length*.—15.61 mm.
*Pistil color*.—Yellow green 150A.
*Anther quantity per flower*.—25.
*Anther length*.—1.57 mm.
*Anther color*.—Yellow 10B.
*Stigma quantity per flower*.—1.
*Stigma length*.—2.36 mm.
*Stigma color*.—Yellow green 150A.
*Style quantity per flower*.—1.
*Style length*.—10.09 mm.
*Style color*.—Yellow green 150A.
*Ovary quantity per flower*.—1.
*Ovary length*.—4.38 mm.
*Ovary diameter*.—4.43 mm.
*Ovary color*.—Yellow green 150A.

Leaves:
*Length*.—120 to 130 mm.
*Width*.—65 to 70 mm.
*Length to width ratio*.—1:1.77.
*Margin*.—Entire to very slightly undulate.
*Color*.—Upper surface — Green 143A; Lower surface — Green 142B.
*Texture*.—Glabrous.
*Leaf shape*.—Elliptic.
*Apex shape*.—Acuminate.
*Base shape*.—Equilateral, cuneate.
*Petiole length*.—20.1 mm.
*Petiole diameter*.—3 mm.
*Petiole color*.—Light green to green 142B.
*Wings*.—Present.
*Wing width*.—12 mm.

Fruit:
*Axial diameter*.—81 to 85 mm.
*Apical diameter*.—79 mm.
*General shape in profile*.—Round.
*Navel*.—Absent to small — 30% 6 to 8 mm.
*Rind color*.—Yellow-orange 21B; compares to color plate 1 of set no. 34 for oranges, where plate 1 is full colored orange and plate 8 is green (Colour Prints for Blemish Standards, Citrus Research Council).
*Oil glands per cm*$^2$.—33.
*Oil gland diameter*.—0.8 to 0.9 mm.
*Rind thickness*.—Thin, 5 to 9 mm.
*Ease of peeling*.—Moderate.
*Rind texture*.—Medium.
*Albedo*.—White.
*Quantity of segments per fruit*.—9 to 11.
*Toughness of segment membrane*.—Tough initially, becoming soft.
*Juice sac length*.—Medium, about 11 to 13 mm.
*Juice sac shape*.—Elongated.
*Juice sac length to width ratio*.—1:4.
*Juice sac color*.—Almost transparent to faint orange.
*Juice soluble solids* (° *Brix*).—13° to 15°.
*Seeds*.—Absent.
*Relative harvest maturity*.—Late.
*Harvest window*.—September.
*Market use*.—Late harvest fresh.

TABLE 1

Fruit internal quality tests

| Date | Color | Fruit Size (mm) | Juice % | TSS | Acid % | Ratio | Average Seed |
|---|---|---|---|---|---|---|---|
| 23 Jul. 2008 | 1-3 | 86-89 | 50.2 | 14.0 | 1.53 | 9.2 | 0 |
| 8 Aug. 2008 | 1 | 81-85 | 55.9 | 14.0 | 1.62 | 8.6 | 0 |
| 21 Aug. 2008 | 1 | 81-85 | 52.3 | 14.7 | 1.48 | 9.9 | 0 |
| 4 Sep. 2008 | 1 | 81-85 | 54.2 | 14.9 | 1.48 | 10.0 | 0 |
| 17 Sep. 2008 | 1 | 81-85 | 54.7 | 14.9 | 1.34 | 11.1 | 0 |
| 16 Jul. 2009 | 1 | 81-85 | 55.1 | 13.1 | 1.29 | 10.2 | 0 |
| 30 Jul. 2009 | 1 | 77-80 | 57.5 | 13.7 | 1.28 | 10.7 | 0 |
| 6 Aug. 2009 | 1 | 77-80 | 51.7 | 13.5 | 1.23 | 11.0 | 0 |
| 17 Aug. 2009 | 1 | 81-85 | 58.4 | 13.4 | 1.21 | 11.1 | 0 |
| 24 Aug. 2009 | 1 | 77-80 | 58.3 | 13.9 | 1.30 | 10.7 | 0 |
| 2 Sep. 2009 | 1 | 77-80 | 59.3 | 14.0 | 1.24 | 11.3 | 0 |
| 10 Sep. 2009 | 1 | 81-85 | 52.0 | 14.8 | 1.03 | 14.4 | 0 |

Color rating: Color transparency rating measured from 1 to 8: 1 = Well colored mature fruit with no green evident; 8 = Green fruit with no signs of color break.
Internal quality tests of fruit of the 'Carninka' navel tree. Fruit from the parent tree, Patensie, South Africa, on 'Swingle' citrumelo rootstock

The invention claimed is:

1. A new and distinct variety of orange tree, substantially as illustrated and described herein.

* * * * *

UNITED STATES PATENT AND TRADEMARK OFFICE

CERTIFICATE OF CORRECTION

PATENT NO. : PP24,934 P3
APPLICATION NO. : 13/385675
DATED : September 30, 2014
INVENTOR(S) : Daniel Frederich Rautenbach It is certified that error appears in the above-identified patent and that said Letters Patent is hereby corrected as shown below:

In the Specification

At column 3, line 41, replace "744" with --7.44--.

Signed and Sealed this
Twenty-seventh Day of January, 2015

Michelle K. Lee

Michelle K. Lee
*Deputy Director of the United States Patent and Trademark Office*